United States Patent [19]
Lauterjung

[11] Patent Number: 5,824,036
[45] Date of Patent: Oct. 20, 1998

[54] STENT FOR INTRALUMINAL GRAFTS AND DEVICE AND METHODS FOR DELIVERING AND ASSEMBLING SAME

[75] Inventor: Karl L. Lauterjung, Munich, Germany

[73] Assignee: Datascope Corp, Montvale, N.J.

[21] Appl. No.: 536,691

[22] Filed: Sep. 29, 1995

[51] Int. Cl.⁶ ........................................... A61F 2/06
[52] U.S. Cl. ............................ 623/1; 606/194; 606/195; 623/11; 623/12; 623/66
[58] Field of Search ..................... 623/1, 11, 12; 606/108, 151, 156, 158, 191, 194, 195, 198, 200

[56] References Cited

U.S. PATENT DOCUMENTS

| | | | |
|---|---|---|---|
| 4,580,568 | 4/1986 | Gianturco | 606/198 |
| 5,282,846 | 2/1994 | Schmitt | 623/12 |
| 5,330,500 | 7/1994 | Song | 623/1 |
| 5,383,887 | 1/1995 | Nadal | 606/198 |
| 5,474,563 | 12/1995 | Myler et al. | 606/195 |
| 5,480,423 | 1/1996 | Ravenscroft et al. | 606/194 |
| 5,509,900 | 4/1996 | Kirkman | 606/198 |
| 5,514,154 | 5/1996 | Lau et al. | 606/194 |
| 5,562,697 | 10/1996 | Christiansen | 623/1 |
| 5,562,724 | 10/1996 | Vorwerk et al. | 623/1 |

Primary Examiner—John G. Weiss
Assistant Examiner—Francis K. Cuddihy
Attorney, Agent, or Firm—J. Gary Mohr

[57] ABSTRACT

A stent graft device for use with a insertion catheter for repair of defects in arteries and other lumens within the body. The stent graft is expandable upon deployment and during deployment the stent graft is retained in a smooth and set position within the artery.

2 Claims, 8 Drawing Sheets

5,824,036

STENT FOR INTRALUMINAL GRAFTS AND DEVICE AND METHODS FOR DELIVERING AND ASSEMBLING SAME

FIELD OF THE INVENTION

The present invention relates to intraluminal stents and grafts, particularly for repairing defects in arteries and other lumens within the body. More particularly, the present invention relates to a device and method for delivering and assembling same in situ for repairing defective body lumens, and particularly abdominal aortic aneurysms.

BACKGROUND OF THE INVENTION

An abdominal aortic aneurysm is a sac caused by an abnormal dilation of the wall of the aorta as it passes through the abdomen. The aorta is the main artery of the body, supplying blood to all organs and parts of the body except the lungs. It arises from the left ventricle of the heart, passes upward, bends over and passes down through the thorax and through the abdomen, and finally divides into the two iliac arteries which supply blood to the pelvis and lower extremities.

The aneurysm ordinarily occurs in the portion of the aorta below the kidneys. When left untreated, the aneurysm will eventually cause the sac to rupture with ensuing fatal hemorrhaging in a very short time. The repair of abdominal aortic aneurysms has typically required major abdominal surgery in which the diseased and aneurysmal segment of the aorta is removed and replaced with a prosthetic device, such as a synthetic graft.

As with all major surgeries, there are many disadvantages to the foregoing surgical technique, the foremost of which is the high mortality and morbidity rate associated with surgical intervention of this magnitude. Other disadvantages of conventional surgical repair include the extensive recovery period associated with such surgery; difficulties in suturing the graft to the aorta; the loss of the existing thrombosis to support and reinforce the graft; the unsuitability of the surgery for many patients, particularly older patients exhibiting co-morbid conditions; and the problems associated with performing the surgical procedure on an emergency basis after the aneurysm has already ruptured.

In view of the foregoing disadvantages of conventional surgical repair techniques, techniques have been developed for repairing abdominal aortic aneurysms by intraluminally delivering an aortic graft to the aneurysm site through the use of a catheter based delivery system, and securing the graft within the aorta using an expandable stent. Since the first documented clinical application of this technique was reported by Parodi et al. in the Annals of Vascular Surgery, volume 5, pages 491–499 (1991), the technique has gained more widespread recognition and is being used more commonly. As vascular surgeons have become more experienced with this endovascular technique, however, certain problems have been encountered. One problem has been the difficult nature of the procedure. Particularly complex is the step of transferring one leg of the graft from one iliac artery to the other, which requires the careful manipulation of numerous catheters and guide wires. Another problem has been the kinking and/or twisting of the graft both during and after the graft has been implanted. Another is fully deploying the stent and graft so that the graft is substantially smooth after being deployed.

There therefore exists a need for a better stent graft system and an implantation method which will overcome the foregoing deficiencies of the prior art. More particularly, there exists a need for a stent and graft system which will more accurately accommodate the widely varying arterial sizes in patients, as well as preventing the graft from kinking. There also exists a need for a method for delivering and implanting the stent and graft which avoids the complex procedure for implanting prior art stent graft systems.

SUMMARY OF THE INVENTION

A stent graft device is disclosed for use with an insertion catheter wherein the device has an expandable stent with various portions of the stent and graft being secured together. Secured to the stent graft is a band or bands and release wire for maintaining and releasing the stent graft from a compressed state. The device also has a holding means for retaining the graft smooth and in a set position when deployed from the insertion catheter as well as means to hold the front portion of the graft from folding back upon itself during deployment from the insertion catheter.

BRIEF DESCRIPTION OF THE DRAWINGS

A more complete appreciation of the subject matter of the present invention and the various advantages thereof can be realized by reference to the following detailed description, in which reference is made to the accompanying drawings in which.

DETAILED DESCRIPTION OF THE PREFERRED EMBODIMENTS

Figure 3:
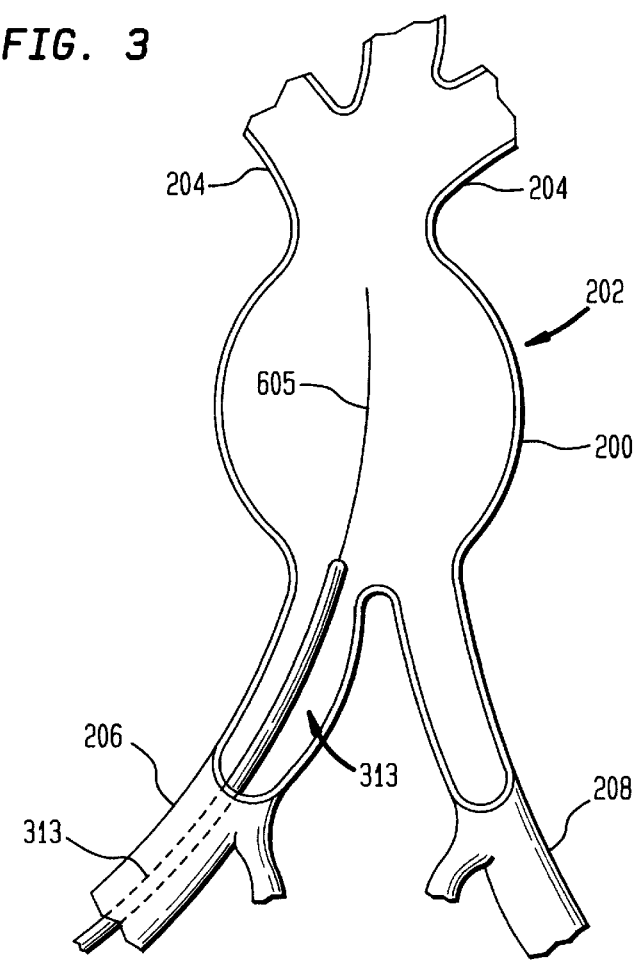
FIG. 3 is a highly schematic partial cross-sectional view of an abdominal aortic aneurysm showing a catheter and guidewire inserted therein as is known in the prior art.

In the detailed description which follows, the features of the present invention will be described in connection with the repair of an abdominal aortic aneurysm. A typical abdominal aortic aneurysm is illustrated in FIG. 3, in which the wall of the aorta 200 is weakened and forms a bulge 202 in the region between the renal arteries 204 and the point at which the aorta 200 branches into the right iliac artery 206 and left iliac artery 208. It will be appreciated, however, that the various features of the present invention may be readily utilized to repair defects in any body lumen which branches into two or more lumens. Indeed, the features of the present invention may be utilized to repair a variety of defects in a body lumen even where the lumen does not have branches associated with it.

Figure 1:
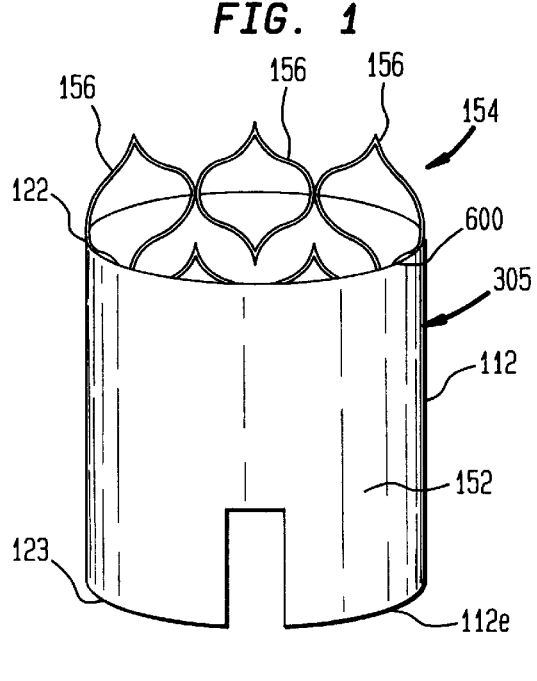
FIG. 1 is a perspective view of a main body of a stent graft for a modular system in accordance with the present invention.
Figure 2:
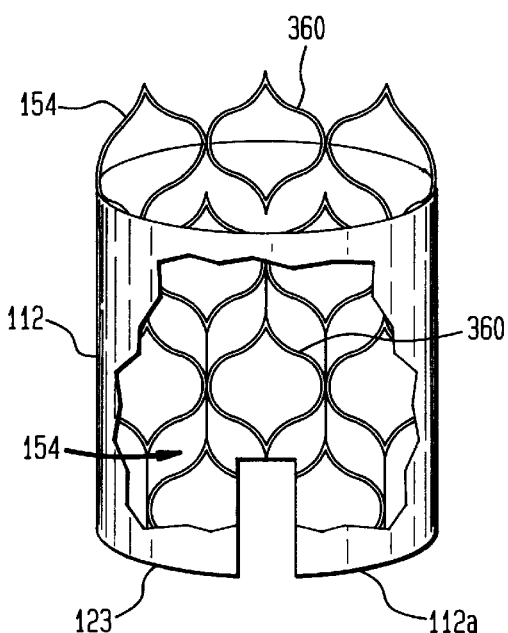
FIG. 2 is a perspective view of the stent graft of the modular system of FIG. 1, partially broken away to reveal the stent structures in the interior thereof in one embodiment of the present invention.
Figure 17:
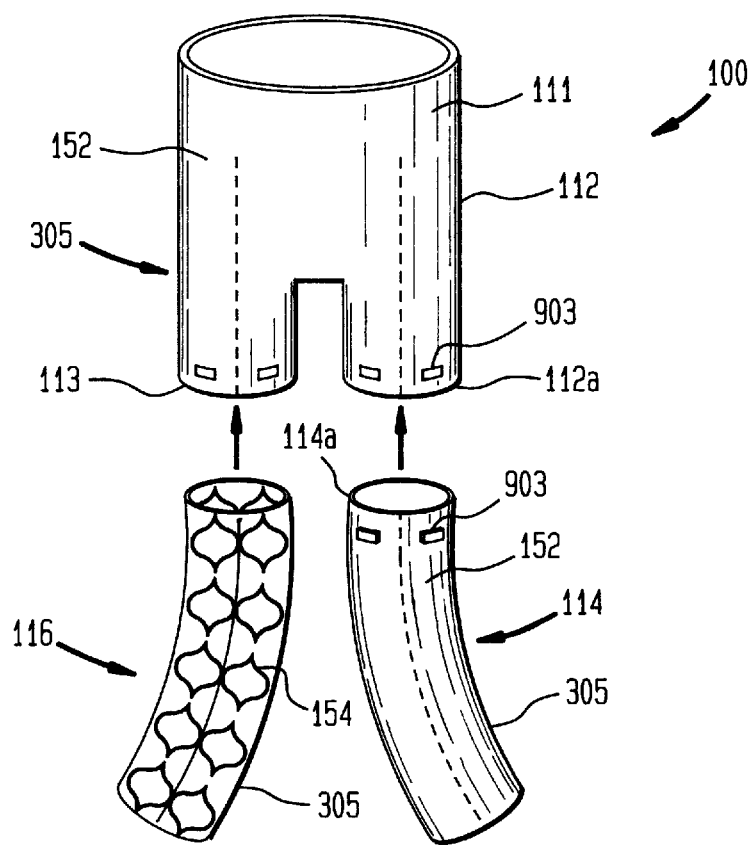
FIG. 17 is a side view of the individual components of the main graft with one of the legs cut away to show the support stent in accordance with the present invention.

Referring to FIG. 17, there is illustrated one embodiment of portions of a modular system 100 for forming a bifurcated stent graft 305 system, it being understood that the term stent graft refers to the combination of a stent 154 and graft, be it graft 112, 114 or 116 or any other combination of a stent and graft, in accordance with one aspect of the present invention. As used herein, the term "modular" refers to the fact that system 100 includes a number of individual components which may be separately delivered by intraluminal techniques to the aneurysm site and then interconnected with one another in situ to form the bifurcated stent graft 305. Each of the components of modular system 100 may be a fully supported structure as shown in FIG. 2, or main graft 112 may only be supported by stent 154 at its proximal circumference 600 as shown in FIG. 1, to provide sufficient strength to permit the in situ construction of the bifurcated graft. In accordance with one embodiment hereof, see FIG. 17, modular system 100 includes, but is not limited to, a main graft 112, first and second leg grafts 114 and 116 respectively, all of which are fabricated as separate components and may be assembled in preselected size combinations depending upon the arterial morphology presented by the patient. Accordingly, each of the various components is preferably provided in a range of sizes sufficient to accommodate the arterial morphology which the surgeon is likely to face in the vast majority of patients.

Main graft 112, as shown in FIG. 1, preferably includes a proximal body portion 111 which contains a stent 154 at least at its proximal circumference 600. The body portion 111 bifurcates to form two separate distal non-communicating channels, 112a and 113 for insertion of legs 114 and 116, see FIG. 17. As used herein, the term "proximal", refers to the end of a component which is upstream or closest to the heart, and the term "distal" refers to the end of a component which is downstream or farthest away from the heart. Main graft 112 may be provided in a number of lengths.

Each leg graft 114 and 116, see FIG. 17, consists of a flexible outer layer 152 which is fully supported internally along substantially its entire length by an expandable stent 154 which assumes a generally cylindrical or tapered configuration in the expanded condition, depending upon the configuration it is given when initially formed. This provides the graft legs 114 and 116 with sufficient structural strength to permit either of them to be inserted in situ within either channel 112a and 113, whichever is appropriate, notwithstanding that said channels 112a and 113 may or may not be fully supported by stent 154. In any of the grafts 112, 114 and 116, stent 154 may protrude beyond the proximal ends 110a, 114a or 116a thereof. The proximal end of any individual cell 360 of rings 309, see FIG. 9, may include one or more barbs 156, see FIG. 1 for anchoring graft 112 to the inside wall of aorta 200 and thereby assist in holding modular assembly 100 in place after it is deployed. The barbs 156 in legs 114 and 116, if used, assist in holding said legs 114 and 116 in place within main graft 112.

Outer layer 152 is preferably formed from a biocompatible material having sufficient strength to withstand the surgical implantation procedure described more fully below and to withstand the blood-flow and other biomechanical forces which will be exerted on modular system 100. Such materials may include, for example, polyester materials, such as DACRON, polytetrafluoroethylene, expanded polytetrafluoroethylene, polyester materials coated with polytetrafluoroethylene, polyurethane, expanded polyurethane and silicone. Outer layers 152 formed from woven materials are preferred. To reduce the bulk and facilitate the intraluminal delivery of grafts 110, 114 and 116, outer layer 152 preferably has a thickness of about 0.1 mm which is about one-third the thickness of conventional graft materials. It will be appreciated, of course, that the present invention can be practiced with other than the stated materials and said other materials may have thickness other than 0.1 mm.

Stents, such as stent 154, may be formed from a wire or the like of a low shape-memory material which has been bent back and forth in a curved pattern in the longitudinal direction of the graft and then wrapped in a circumferential direction transverse to the longitudinal direction to form one or more loops of a predetermined circumference. As used herein, the term "low shape-memory material" refers to a material that, once deformed from an initial shape to a subsequent shape, will tend to maintain the subsequent shape and not return to the initial shape. Such materials preferably include biocompatible metals, including, for example, stainless steel, titanium, tantalum, gold, platinum, copper and the like, as well as alloys of these metals. Biocompatible low shape-memory plastics may also be used to form stents. Alternatively, stents may be formed from a high shape-memory plastic or alloy, such as nitinol, which automatically transforms from one shape to another shape as its temperature passes through a critical point.

A stent of the above type is disclosed in commonly assigned U.S. patent application Ser. No. 08/353,066 entitled "High Hoop Strength Intraluminal Stent".

Figure 5:
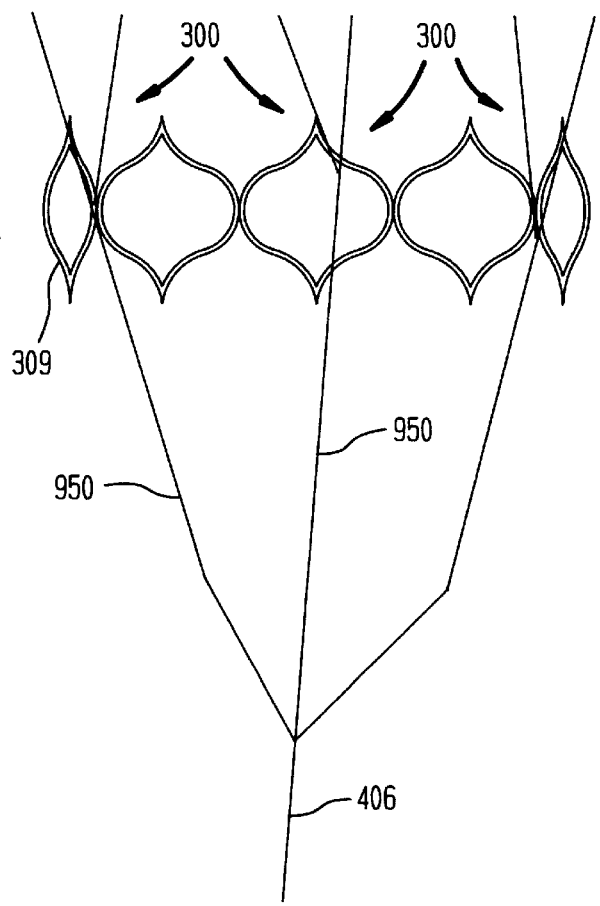
FIG. 5 is a side view of the forks and fork wire in accordance with the present invention.
Figure 8:
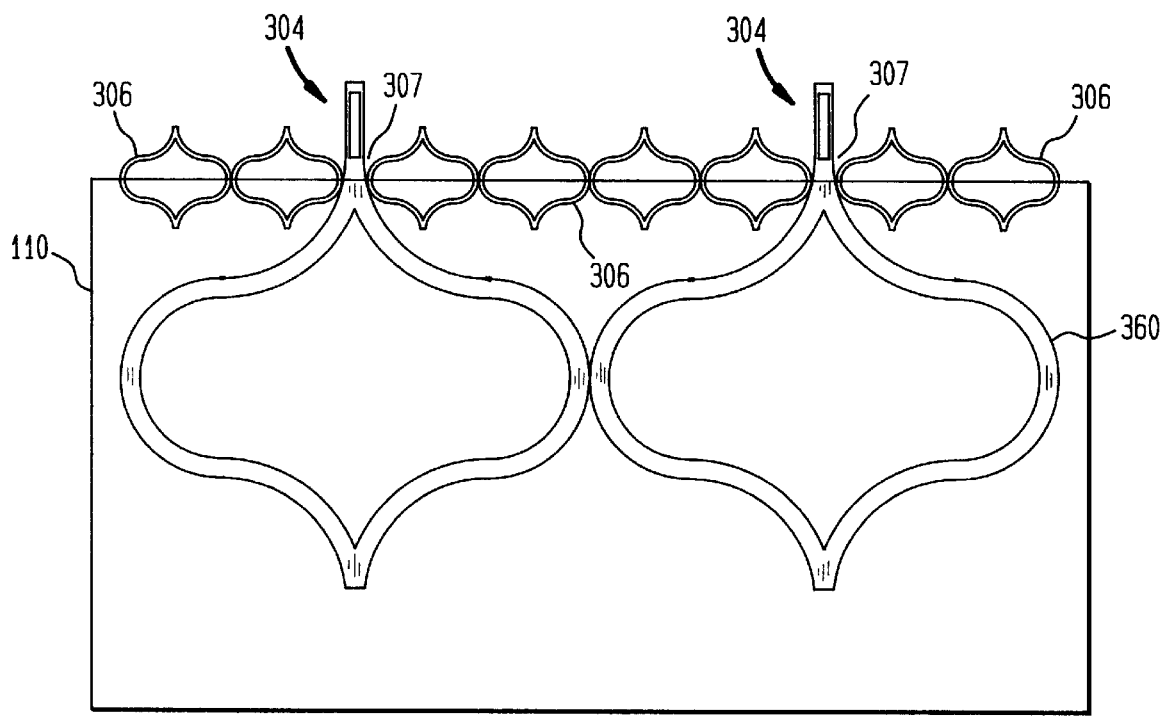
FIG. 8 is a side view of the main stent and smaller end connecting stents in accordance with the present invention.
Figure 9:
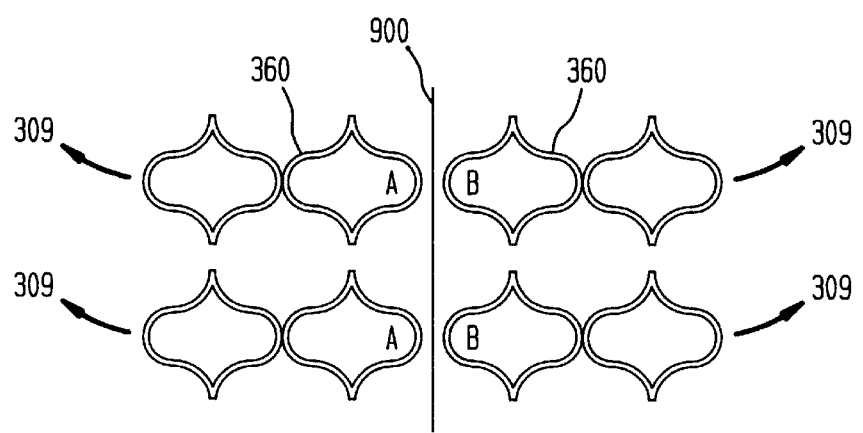
FIG. 9 is a side view of a ring assembly of the individual ring stent components in accordance with the present invention.
Figure 9A:
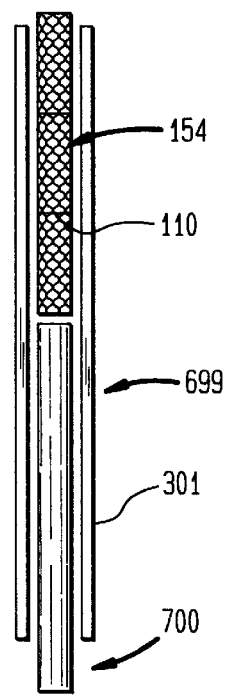
FIG. 9a is a prior art system for pushing the stent graft from the sheath in accordance with the present invention.

However, in the above application as in other such applications as shown in FIG. 9a, the stent is being pushed out of the applicator 699, by the pusher 700 held in a fixed position as the outer sheath 301 is pulled back, this creates the disadvantages of compressing the stent graft 305 while it is inside sheath 301, thereby resulting in an increase in diameter of stent graft 305 and necessitating a greater force to remove stent graft 305 from sheath 301. Therefore, unlike prior stents and the stent disclosed in the previously cited co-pending patent application, stent 154 used with grafts 112, 114 and 116 of the present invention has atraumatic forks 300 as shown in FIG. 5 to allow stent 154 to be pulled from the sheath 301 as opposed to pushed. While forks 300 are shown in a "V" type configuration, they may be formed in any type of configuration, known in the art, that would cooperate with eyes 304, see FIG. 8, to have the net effect of pulling the stent graft 305 out of sheath 301. After stent 154, with a graft secured to it leaves outer sheath 301, see FIG. 6, and the stent 154 and graft fully deploy and expand to cling to the arterial wall, forks 300, no longer being needed to retain the front portion of the stent graft 305 in place, can be retracted without displacement of the stent graft 305, since the clinging force to the arterial wall of stent 154 is much higher than the sliding force of the retracting forks 300 moving over the internal portion of the stent graft 305.

Figure 6:
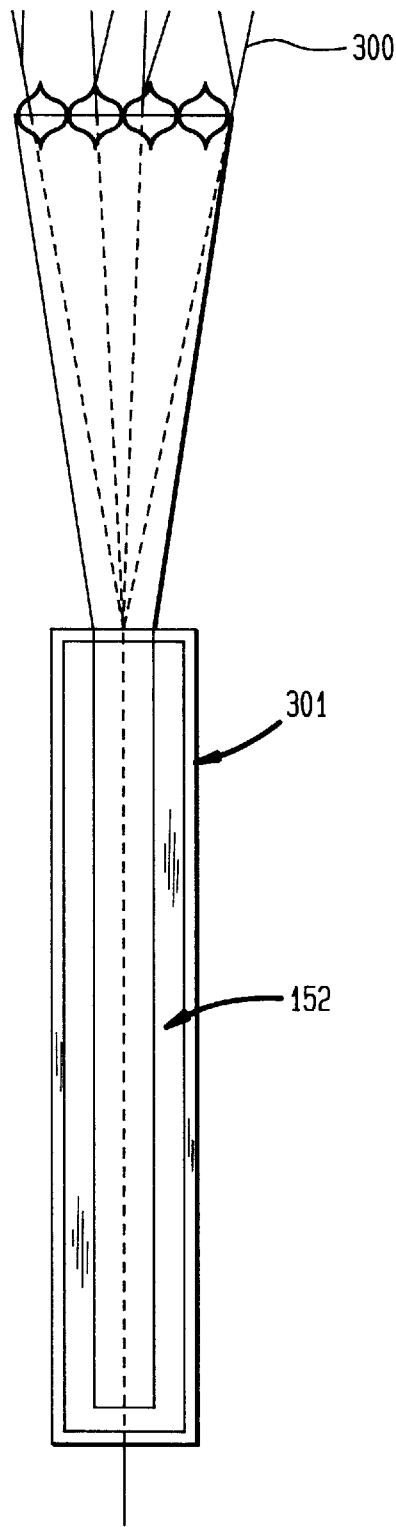
FIG. 6 is a side view of the stent graft partially deployed from the sheath in accordance with the present invention.
Figure 7:
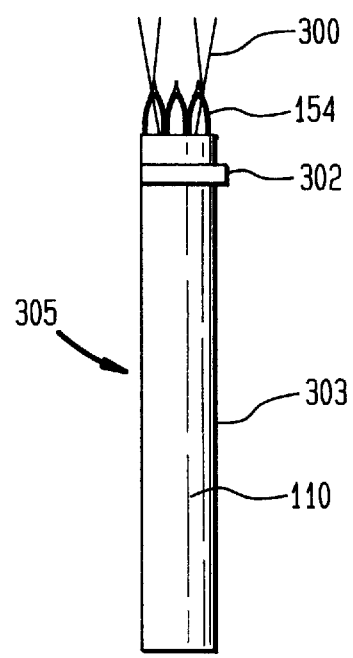
FIG. 7 is a side view of the graft with a compression band and release wire attached in accordance with the present invention.

To allow forks 300 to pull graft 112, 114 or 116 and stent 154 from sheath 301, the proximal portion of stent 154 which is first deployed from sheath 301, contains eyes 304, see FIG. 8, into which the forks 300 are inserted so that the compressed stent graft 305, see FIGS. 6 and 7, is activated, forks 300 being inserted into eyes 304, see FIG. 8, to retain stent 154, when any of grafts 112, 114 or 116 are attached, in a set position, within the lumen being repaired, as outer sheath 301 is retracted from that set position within the lumen being repaired. Once fully deployed from outer sheath 301, graft 112, 114 or 116 and stent 154, still being constrained at their front portion by band 302 or at other locations, not shown, by one or more additional bands 302 or by securing means known in the art, can be easily positioned by the user within the artery, since at the front portion of graft 112, 114 or 116 and stent 154 is maintained at a smaller diameter than the inside of the artery by band 302. Once stent 154 is properly positioned by the user, a release wire 303 is used to disengage band 302 from around stent 154. To facilitate the releasing of band 302, band 302 may be perforated prior to being place over any of grafts 112, 114 or 116, but it does not have to be, since there are many ways in the art to release band 302 by wire 303. The release of band 302 allows stent 154 to expand and thereby expand the graft to which it is attached until a tight seal is formed between the attached graft and the inside of the artery or the inside of the graft to which it is being joined. It is at this point that forks 300 are retracted and slid through the interior of stent 154 causing a slight force to be applied toward the outer sheath 301. This can be done without disturbing the positioning of the stent 154 or the graft to which it is attached, since the clinging force to the arterial wall of the stent 154 is much higher than the sliding force of the retracting forks 300. In this manner, the graft material 152 is straightened by the retraction of outer sheath 301, since the forks 300, while still being in place, hold the fabric 152 of the graft in place while the movement of outer sheath 301 over the outer portion of the stent graft 305. In addition, further smoothing of the stent graft 305 is accomplished by the movement of forks 300, once released, over the internal portion of the stent graft 305.

As shown in FIG. 8, stent 154 has a boundary ring set 306, which may be of the same configuration as the make up of rings 309 of stent 154, but of smaller dimension. This boundary ring set 306 supports graft 112, 114 or 116 in those areas of graft between the tip portions 307 of stent 154 thereby preventing the graft from flapping back upon itself.

Figure 10:
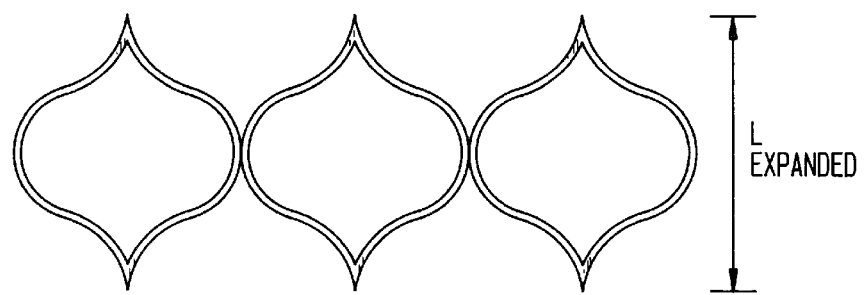
FIG. 10 is a side view of a stent ring in its expanded position in accordance with the present invention.
Figure 11:
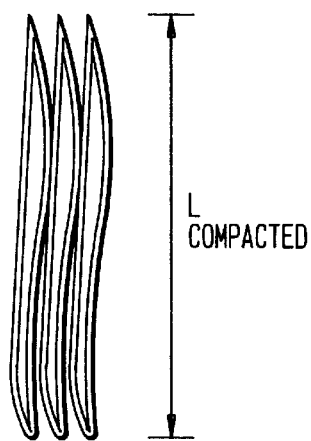
FIG. 11 is a side view of a stent ring in its compacted position in accordance with the present invention.
Figure 12:
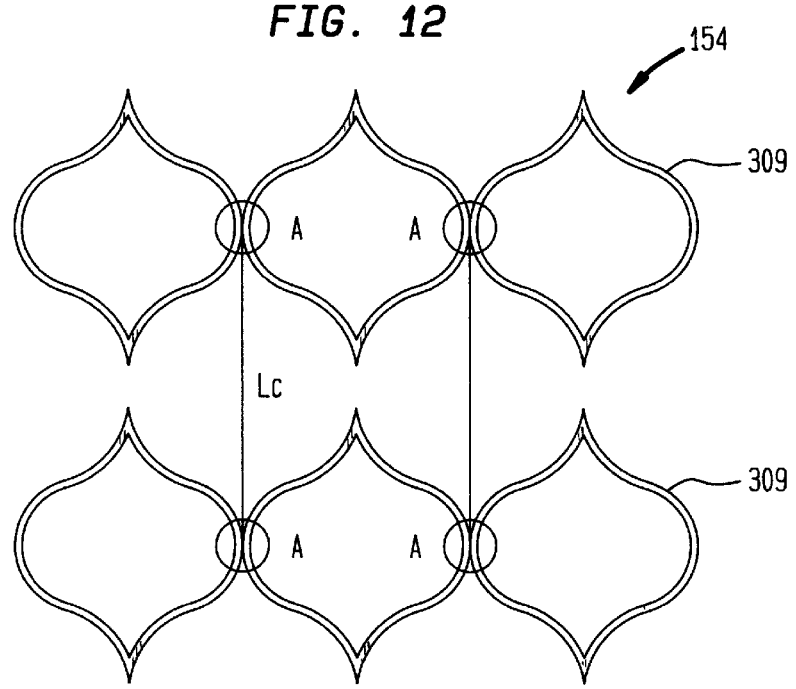
FIG. 12 is a side view of two ring sections connected at the tangent point of a cell of the ring in accordance with the present invention.
Figure 13:
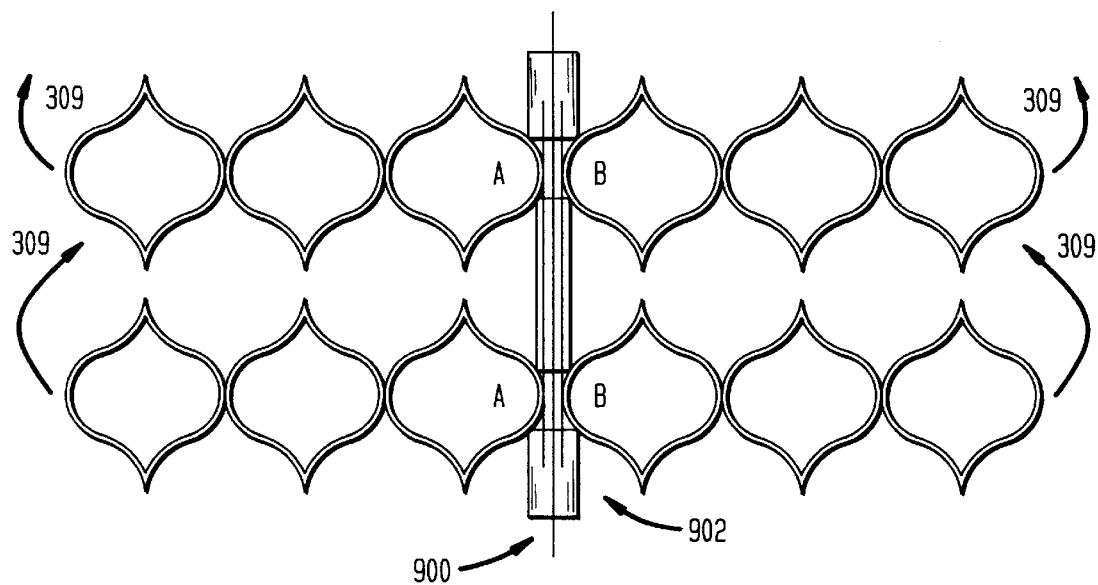
FIG. 13 is a side view of two ring sections connected by heat shrink in accordance with the present invention.
Figure 16:
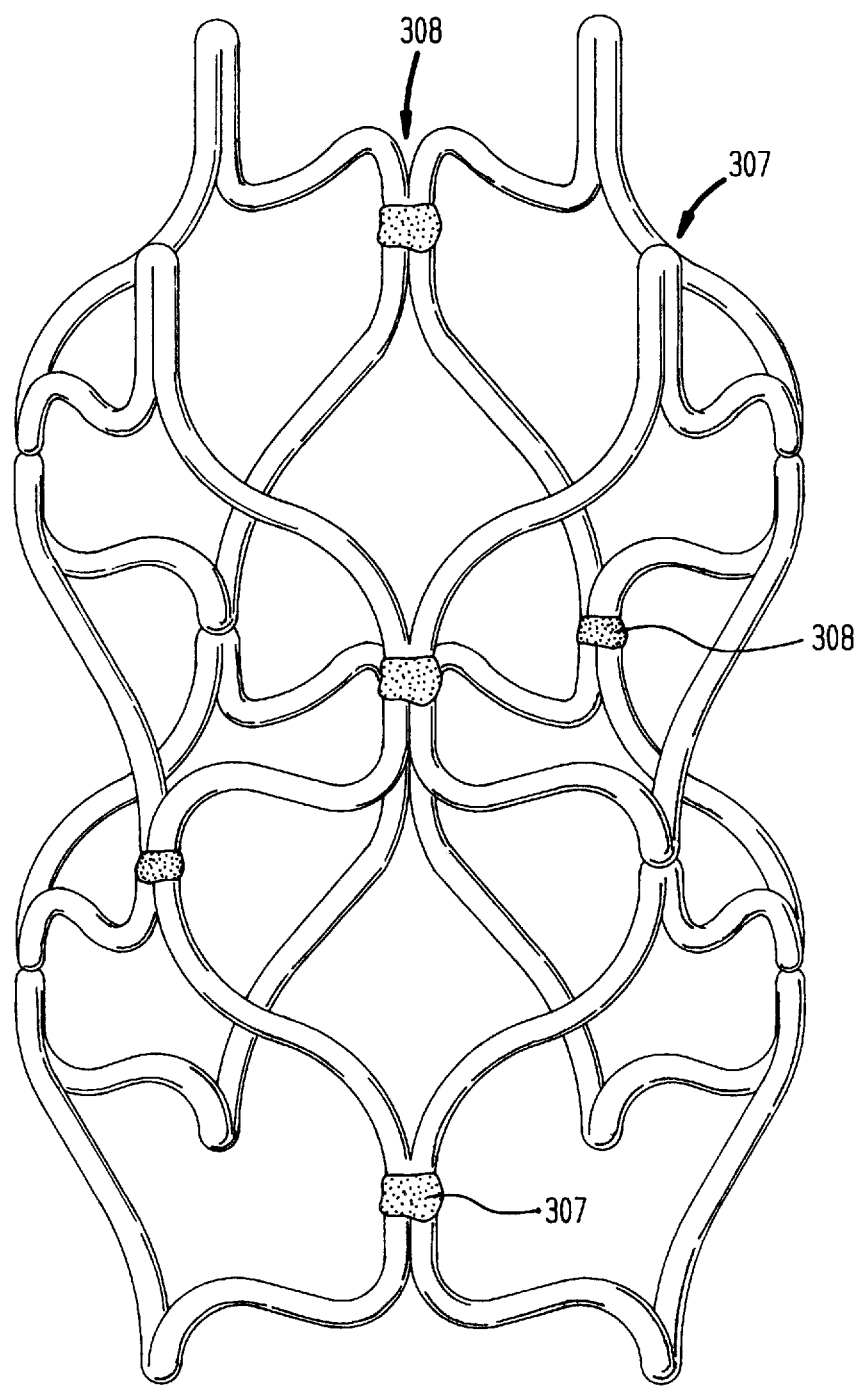
FIG. 16 is perspective view of the stent of the referred to co-pending application showing the connection points between the cells of the ring and the rings.

As shown in co-pending application Ser. No. 08/353,066 that stent is interconnected as shown in FIG. 16, by both its tip portions 307 and its tangent portions 308. Compacting a stent, when constructed in the heretofore mentioned manner, for the purpose of inserting it into sheath 301 expands the length of such a stent proportionately with the number of stent rings 309, see FIG. 9. As shown in FIGS. 10 and 11, length expanded is less than length contracted and total elongation is equivalent to the number of rings multiplied by the dimension of "L" compacted. This cumulative elongation of each ring elongates to a point that makes it more difficult to position within the artery due to its expanded length and shortening upon deployment. However, if stent 154 is connected only at points A as shown in FIG. 12, or at points A and B as shown in FIG. 13 which maintains each ring 309 of stent 154 a certain distance apart, it reduces the cumulative elongation during packing and deployment, which eases targeting the stent graft 305.

Connecting the rings 309 of stent 154 may be accomplished in various ways as is known in the art, however, as shown in FIG. 9, a preferred way is to laser weld points tangent points A and B of each cell 360 of each ring 309 with a connecting wire 900, preferably of the same material as the sent 154. An alternative to this is to heat shrink the connection by wrapping wire 900 with a heat shrinkable material so that rings 309 are secured at points A and B when heat is applied to the heat shrinkable material as is shown in FIG. 13. A further alternative is to cut the form as shown in FIG. 9 as a whole unit and subsequently secure the joining members by welding, bonding or other known method.

Figure 4:
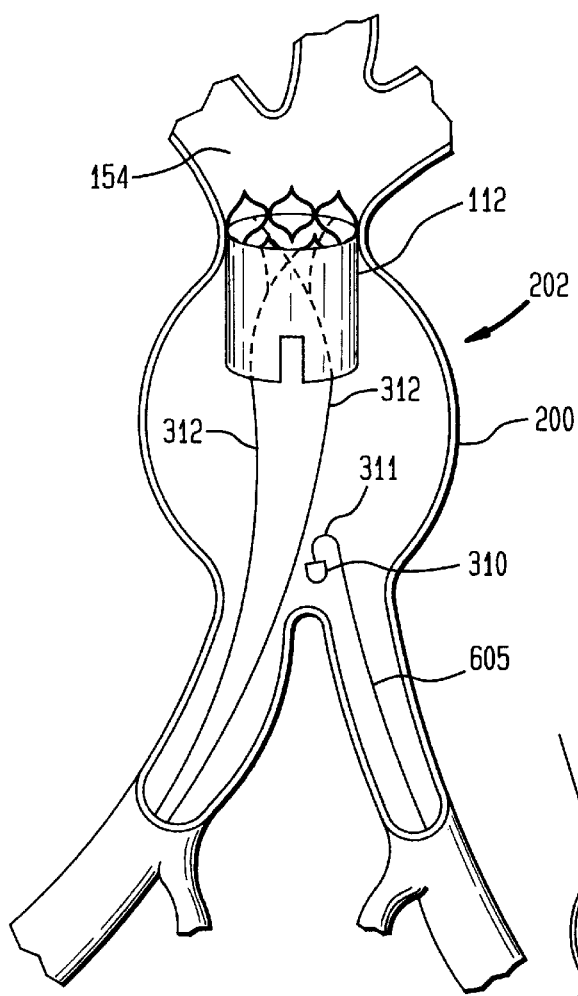
FIG. 4 is a side view showing the locating magnetic tip in accordance with the present invention.

As shown in FIG. 4, the wire 312 attached to forks 300 is preferably a drawn wire of magnetic steel. The individual wires 312 and forks 300 that are used in any procedure may be of different sizes in order for the user to easily identify the individual wires 312 and forks 300 being used in the procedure. To further distinguish the individual wires, they may be color coated at their distal ends.

Figure 14:
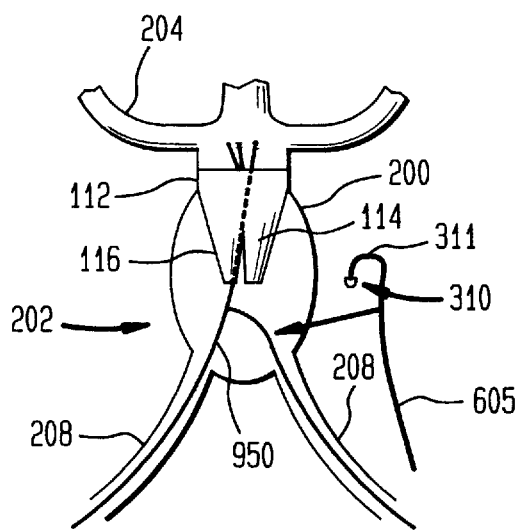
FIG. 14 is a side view of the inserted magnetic guide wire tip adhered to the fork wire in accordance with the present invention.
Figure 15:
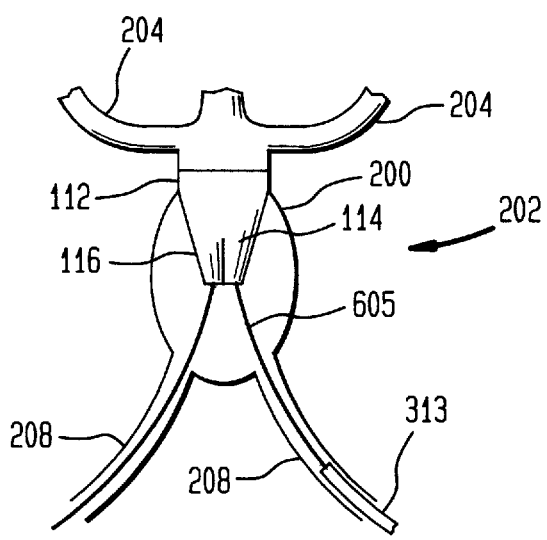
FIG. 15 is a side view of the introducer catheter being inserted over the positioned guide wire in accordance with the present invention.

When the bifurcated stent graft 305 is to be used, in order to aide in positioning the different legs 114 and 116 which are usually overdimensioned to ensure proper fit within the distal ends 112a and 113 of main graft 112, as shown in FIG. 17 all the component parts of the total stent graft 305 system may have electrically dense materials 903 or other detectable materials at key points so that the user can establish the location of each part of the stent graft 305 during the positioning process. To further aide in positioning of legs 114 and 116 of the stent graft 305, a magnetic tip 310, as shown in FIG. 4, preferably of Nd-Fe-B material, is attached to the flexible end 311 of a guide wire 605, see FIG. 14. Under fluoroscopic guidance, when guide wire 605 is inserted into the contralateral femoral artery, notwithstanding which artery is first used to deploy a leg of the stent graft 305, guide wire 605 is moved until magnetic tip 310 comes into contact with the wire base 950 of fork 300, it being understood that in this procedure at least one fork 300 is not retracted so that it may be used as a guide, see FIG. 4. Once magnetic tip 310 is in contact with the wire base 950 of fork 300, magnetic tip 310 is advanced up said wire 950 until it is in position inside bifurcated stent graft 305 body 112 at which time fork wire 300 may be removed, see FIG. 14. The introducer catheter 313, see FIG. 15, is then inserted over guidewire 605 until it makes contact with the flexible end 311 of guidewire 605 thereby assuring that either leg 114 or 116 is properly located in either channel 112a or 113 of main graft 112.

Although the invention herein has been described with reference to a particular embodiment, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A stent graft device for insertion into a lumen by an insertion catheter comprising:

an expandable stent having multiple recurring sections, a graft secured to said stent, a band for preventing the stent and the graft from expanding, a release means for severing the band to allow the stent and the graft to expand, means for retaining the stent and the graft in a set position while removing the stent and graft from an insertion catheter, said retaining means including a) a fork shaped means in a form of a letter V for engaging the stent, b) receiving means on the stent having a shape of an eye opening of a sewing needle for receiving the fork shaped means, and c) a fork control means for retaining and moving the forks by manipulation of a wire attached to the fork shaped means with said wire extending out from both ends of the insertion catheter, means for securing the multiple recurring sections of the stent to each other, means for retaining an outer surface of the graft substantially in one plane as the insertion catheter is removed from the stent and the graft, and means for holding a front portion of the graft from folding back upon itself during deployment from the insertion catheter.

2. A stent graft device for insertion into a lumen by an insertion catheter comprising:

an expandable stent having at least a first set of rings of multiple cells and multiple recurring sections, a graft secured to said stent, a band for preventing the stent and the graft from expanding, a release means for severing the band to allow the stent and the graft to expand, means for retaining the stent and the graft in a set position while removing the stent and graft from an insertion catheter, means for securing the multiple recurring sections of the stent to each other, means for retaining an outer surface of the graft substantially in one plane as the insertion catheter is removed from the stent and the graft, and means for holding a front portion of the graft from folding back upon itself during deployment from the insertion catheter including a second set of rings having cells of lesser area than the cells of the first rings and connected to the cells at a position where each individual cell is farthest from an adjacent cell.

* * * * *